United States Patent [19]

Marcus

[11] Patent Number: 5,549,903
[45] Date of Patent: Aug. 27, 1996

[54] MICROENCAPSULATED COMPOSITION CONTAINING CHLORPYRIFOS OR ENDOSULFSAN

[75] Inventor: Arie Marcus, Beer Sheva, Israel

[73] Assignee: Ben Gurion University of Negev Research & Development Aurthority, Beer Sheva, Israel

[21] Appl. No.: 281,677

[22] Filed: Jul. 28, 1994

[51] Int. Cl.$^6$ ............................................. A01N 25/28
[52] U.S. Cl. ............................................. 424/408; 424/405
[58] Field of Search ...................... 424/408, 405

[56]  References Cited

U.S. PATENT DOCUMENTS

| | | | |
|---|---|---|---|
| 2,168,064 | 8/1939 | Falcon | 424/617 |
| 2,800,458 | 7/1957 | Green | 424/492 |
| 3,063,893 | 11/1962 | Goldberg et al. | 514/70 |
| 3,069,370 | 12/1962 | Jensen et al. | 427/213.3 |
| 3,098,000 | 7/1963 | Harrison | 514/762 |
| 3,116,216 | 12/1963 | Demain | 435/244 |
| 3,130,121 | 4/1964 | Rapport | 424/418 |
| 3,137,631 | 6/1964 | Soloway | 424/491 |
| 3,264,176 | 8/1966 | Rapport | 424/125 |
| 3,270,100 | 8/1966 | Jolkovski et al. | 264/4 |
| 3,418,250 | 12/1968 | Vasiliades | 424/497 |
| 3,429,827 | 2/1969 | Ruus | 264/4.7 |
| 3,541,203 | 11/1970 | Fogle et al. | 424/464 |
| 3,560,613 | 2/1971 | Miskus et al. | 514/68 |
| 3,577,515 | 5/1971 | Vandegaer | 424/497 |
| 3,839,561 | 10/1974 | Bordenca | 424/59 |
| 3,959,464 | 5/1976 | Desavigny | 424/419 |
| 4,056,610 | 11/1977 | Barber, Jr. et al. | 424/405 |
| 4,230,809 | 10/1980 | Heinrich et al. | 424/499 |
| 4,417,916 | 11/1983 | Beestman et al. | 424/497 |
| 4,497,793 | 2/1985 | Simkin | 264/4.7 |
| 4,563,212 | 1/1986 | Becher et al. | 71/11 |
| 4,666,747 | 5/1987 | Quinn | 514/65 |
| 4,888,174 | 12/1989 | Farquharsun et al. | 424/405 |
| 5,317,004 | 5/1994 | Misselbrook et al. | 504/116 |

FOREIGN PATENT DOCUMENTS

| | | |
|---|---|---|
| 0140548 | 5/1985 | European Pat. Off. . |
| 0148169 | 7/1985 | European Pat. Off. . |
| 0165227 | 12/1985 | European Pat. Off. . |
| 1371179 | 10/1974 | United Kingdom . |

Primary Examiner—Thurman K. Page
Assistant Examiner—P. Webber
Attorney, Agent, or Firm—Browdy and Neimark

[57] ABSTRACT

The present invention relates to a microencapsulated chlorpyrifos or endosulfan composition comprising a polyurea shell and one or more photostable ultraviolet and visible light absorbent compound having a log molar extinction coefficient of from about 2 to 5 with respect to radiation having wave lengths in the range of about 310 to 450 nanometers, wherein said photostable ultraviolet and visible light absorbent compound does not react with the monomer used in building the polyurea shell. The result is a microencapsulated composition having unexpected long, extended insecticidal activity with high toxicity to target species and very low toxicity to non-target animals.

20 Claims, No Drawings

MICROENCAPSULATED COMPOSITION CONTAINING CHLORPYRIFOS OR ENDOSULFSAN

BACKGROUND OF THE INVENTION

The present in vent ion relates to microencapsulated insecticide compositions which are stabilized against environmental degradation. The present invention more specifically relates to microencapsulated chlorpyrifos or endosulfan stabilized against degradation by visible and ultra-violet light having unexpected extended insecticidal activity while having unexpected low toxicity to non-target species.

Chlorpyrifos, which is the common name for O,O-diethyl-O-( 3,5,6-trichloro-2-pyridyl)-phosphorathio- ate, is a well-known insecticide. Two major problems of this insecticide is on the one hand its ease of decomposition when exposed to the environment and the concomitant high toxicity to non-target animals. Thus, technical chlorpyrifos has a toxicity to rats (acute oral) of an $LD_{50}$ of 168 mg/kg and a toxicity to trout (acute) of an $LC_{50}$ of 0.007 mg/kg.

Endosulfan, which is the common name for 6,7,8,9,10-hexachloro- 1,5-5a,9a tetryhydro-6,9-methano- 2,4,3-benzodioxathipia-3-oxide, is also a well-known insecticide, with stability and toxicity problems. Its toxicity problem is most acute to non-target species such as fish and bees as the technical material has an $LD_{50}$ to non-target species such as mice of 30 mg/kg. For an EC formulation to classified as "only harmful" its $LD_{50}$ to mice must be at least 200 mg/kg. However, to reach such a toxicity, the concentration of endosulfan must be dropped to 3%, resulting in a non-economical mixture of very low activity.

The microencapsulation of pesticides and insecticides has been proposed in the prior art as a way of extending the insecticidal life of pesticides while supposedly decreasing their toxicity to non-target animals. Examples are: U.S. Pat. Nos. 2,800,458; 3,069,370 , 3,116,216, 3,137,631, 3,270, 100; 3,418,250; 3,429,827; 3,577,515; 3,959,164; 4,417, 916; and 4,563,212. British Patent Number 1,371,179; European Patent Publication Numbers 148,169 and 165,227; and Israel Patent Numbers 79,575 and 84,910.

Microencapsulated chlorpyrifos has been reported in European Patent Application No. 140,548. Microencapsulated endosulfan has been reported in U.S. Pat. No. 4,230, 809. in neither case is there any report of the use of ultraviolet absorbers in these microencapsulated formulations.

The use of an ultraviolet absorber to protect insecticides, especially pyrethroids, has been reported in U.S. Pat. Nos. 2,168,064; 3,063,893; 3,098,000; 3,130,121; 3,264,176; 3,541,203; 3,560,613; and 3,839,561.

U.S. Pat. Nos. 4,056,610 and 4,497,793 describe the use of specific UV absorbers in microencapsulated pyrethrins. However, these require the case of U.S. Pat. No. 4,056, 610—the use of a UV absorber both the outer casing and in the liquid fill.

Regardless of the disclosure in the prior art, there has not yet been offered for sale microencapsulated chlorpyrifos or endosulfan, which has both extended insecticidal activity and extremely low toxicity to non-target animals.

SUMMARY OF THE INVENTION

According to the present invention there is provided a microencapsulated chlorpyrifos or endosulfan composition comprising a polyurea shell and one or more photostable ultraviolet and visible light absorbent compounds having a log molar extinction coefficient of from about 2 to 5 with respect to radiation having wave lengths in the range of about 310 to 450 nanometers wherein said photostable ultraviolet and visible light absorbent compound does not react with the monomer used in building the polyurea shell. The result is a microencapsulated composition having unexpected long, extended insecticidal activity with high toxicity to target species and very low toxicity to non-target animals.

DETAILED DESCRIPTION OF THE INVENTION

The microencapsulated insecticidal composition of the present inventions are prepared using standard processes. Details for chlorpyrifos appear in Example 1. Details for endosulfan appear in Example 10. The percentage of the envelope—excluding the water and the polyvinyl-alcohol varies from 3% to 50%, preferably up to 30%. Similarly, the fill contains from 0.5% to 5% preferably 1% to 3%, of the photostable ultraviolet and visible light absorbent compound.

Details of the stability of chlorpyrifos are listed in Example 2. For endosulfan, it was found that it decomposed after irradiation for 100 hours at 310±5 nanometers and 475± nanometers.

The photostable ultraviolet and visible light absorbent compounds are selected from the group consisting of sterically hindered amines and dyes. The sterically hindered amines are in turn selected from the Ciba-Geigy products known by the general trade name "TINUVIN" where the preferred ones are "TINUVIN -770" and "TINUVIN - 780" having the following structures and Chemical Abstract Numbers as follows:

"TINUVIN-770"

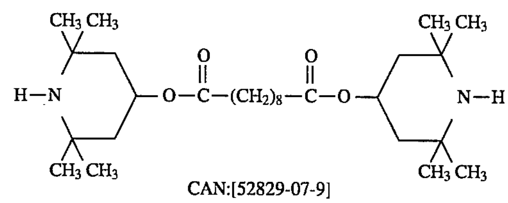

CAN:[52829-07-9]

"TINUVIN-780"

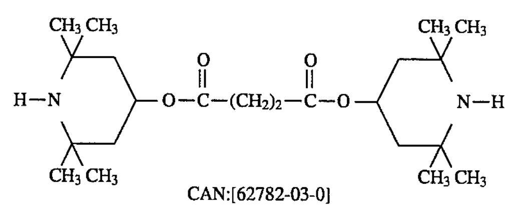

CAN:[62782-03-0]

Designation: Butanedioic acid, bis-(2,2,6,6-tetramethyl-4-piperidinyl) ester

These ultraviolet and visible light absorbent compound were chosen among other reasons because they did not react with the monomers that build the envelope.

The microencapsulated compositions of the invention may also optionally contain in addition to one of the "TINUVINS" dyes selected from the group consisting of Thermoplast green, Blue paste, Fluorescein, Sudan blue, Macrolex blue and Sedan III.

The microencapsulated compositions containing chlorpyrifos are listed in Table 1. Several of these compositions were studied to determine which had the longest activity against larger species, such as beetles and cockroaches, even after exposure to sunlight, (Examples 4,5 and 8) while having the lowest toxicity to non-target species, represented by mice, fish and bees (Examples 3,6 and 9). The result was that composition Numbers 14 and 15 containing chlorpyrifos were the preferred compositions, with Number 14 most preferred.

Almost all of the microencapsulated compositions of the present invention containing endosulfan gave poor toxicological results on mice. That is, in order to obtain a formulation with an $LD_{50}$ of 200 for mice the formulation would have to be very diluted; making it commercially unacceptable. However, compositions numbers 59 and 61 showed appreciably lower toxicity to non-target species at a commercially viable concentration of endosulfan, with number 61 the best. Examples 11 and 12 show the toxicity of these two formulations against the non-target species represented by mice and fish, respectively.

Thus, the present invention affords a novel microencapsulated composition containing chlorpyrifos or endosulfan, which not only can withstand relatively long exposure to sunlight, has a low toxicity to non-target species such as mice, bees and fish, while retaining commercially acceptable toxicity levels to target species such as beetles and cockroaches.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention, as defined by the appended claims. Thus, the following examples, which include preferred embodiments, will serve to illustrate the practice of this invention, it being understood that the particulars shown are by way of example and for purposes of illustrate discussions of preferred embodiments of the present invention only and are presented in the cause of providing what is believed to be the most useful and readily understood description of procedures as well as of the principles and conceptual aspects of the invention.

EXAMPLE 1

Representative Preparation of the Microencapsulation of Chlorpyrifos

Four separate solutions: A, B, C and D were prepared as follows:

| | |
|---|---|
| Solution A: | 1520 ml water |
| | 15.2 g polyvinylalcohol ("MOWIOL-G-4) |
| Solution B: | 720 g melted chlorpyrifos |
| | 140 g Voranate M-580 |
| | 4 g "TINUVIN-770" |
| Solution C: | 360 ml water |
| | 20 g ethylene diamine |
| | 18.3 g diethylenetriamine |
| Solution D: | 14 g propylene glycol |
| | 58.4 Nonylphenol 6 mole ethoxylated (NP-6) |
| | 10 g xanthan gum |

Formation of the microcapsules is carried out by interfacial polymerization as follows:

A good emulsion of Solution B in A was made by mixing for 5 minutes in a high sheer mixer, keeping the mixture at 40° C. To this emulsion was slowly added Solution C, keeping the temperature at 40° C. The reaction mixture was cooled to 25° C. to 35° C. and the stirring was continued for 4 additional hours. Solution D was added and the mixture stirred for 15 minutes. Representative microencapsulated compositions of chlorpyrifos are listed in Table 1.

TABLE 1

REPRESENTATIVE MICROENCAPSULATED COMPOSITIONS OF CHLORPYRIFOS

| Formulation no. | isocyanates types | amount | E.D.A. (g) | DETA (g) | PDA (g) | Tinuvin 770 (g) | TEPA (g) | Tinuvin P (g) | $TiO_2$ (g) | Escalol (g) | Water (ml.) | PV (g) |
|---|---|---|---|---|---|---|---|---|---|---|---|---|
| 1. | ISONATE M-309 | 35 | 6.2 | 5.7 | — | 0.9 | — | — | — | — | 360 | 4 |
| 2. | ISONATE M-302 | 35 | 6.2 | 5.7 | — | — | | — | 1 | — | 360 | |
| 3. | ISONATE M-302 | 35 | — | 5.7 | — | — | 9.6 | — | — | 1 | 360 | |
| 4. | ISONATE M-302 | 35 | — | 5.7 | — | 0.9 | 9.6 | — | — | — | 360 | 4 |
| 5. | ISONATE M-302 | 35 | 6.2 | 5.7 | — | 0.9 | — | — | — | — | 380 | 3.8 |
| 6. | Voranate M-580 | 35 | — | 5.7 | 7.7 | 0.9 | — | — | — | — | 380 | 3.8 |
| 7. | Voranate m-220 | 35 | 6.2 | 5.7 | — | 0.9 | — | — | — | — | 380 | 3.8 |
| 8. | HMDI | 2.61 | 6.1 | 5.7 | — | — | — | 1 | — | — | 360 | 6 |
| 9. | HMDI | 2.61 | 6.2 | 5.7 | — | — | — | — | 1 | — | 360 | .6 |
| 10. | TDI | 27 | 6.2 | 5.7 | — | — | — | 1 | — | — | 360 | 3.6 |
| 11. | TDI | 27 | 6.2 | 5.7 | — | 1 | — | — | — | — | 360 | 3.6 |
| 12. | TDI | 27 | — | 5.7 | — | — | 9.6 | 1 | — | — | 360 | 3.6 |
| 13. | Voranate M-580 | 35 | 6.2 | 5.7 | — | — | — | 1 | — | — | 360 | 3.6 |
| 14. | Vorante M-580 | 35 | 6.2 | 5.7 | — | 0.9 | — | — | — | — | 400 | 4 |
| 15. | Voranate M-580 | 280 | 39.7 | 36.8 | — | 8 | — | — | — | — | 3040 | 30.4 |
| 16. | Voranate M-580 | 280 | 39.7 | 36.8 | — | 8 | — | — | — | — | 3040 | 30.4 |
| 17. | Voranate | 280 | 39.7 | 36.8 | — | 8 | — | — | — | — | 3500 | 35 |

TABLE 1-continued

REPRESENTATIVE MICROENCAPSULATED COMPOSITIONS OF CHLORPYRIFOS

| Formulation no. | isocyanates types | amount | E.D.A. (g) | DETA (g) | PDA (g) | Tinuvin 770 (g) | TEPA (g) | Tinuvin P (g) | TiO$_2$ (g) | Escalol (g) | Water (ml.) | PV (g) |
|---|---|---|---|---|---|---|---|---|---|---|---|---|
| 18. | Voranate M-580 | 280 | 34.7 | 31.9 | — | 9 | — | — | — | — | 3040 | 30.4 |
| 19. | Voranate M-580 | 4.4 | 0.62 | 0.58 | — | 1 | — | — | — | — | 380 | 3.8 |
| 20. | Voranate M-580 | 35 | 4.2 | 4 | — | 1 | — | — | — | — | 380 | 3.8 |
| 21. | Voranate M-580 | 140 | 20 | 18.3 | — | 4 | — | — | — | — | 1520 | 15.2 |
| 22. | Voranate M-580 | 35 | 5.6 | 5.3 | — | 1 | — | — | — | — | 380 | 3.8 |
| 23. | Voranate M-580 | 35 | 5.6 | 5.3 | — | 1 | — | — | — | — | 380 | 3.8 |
| 24. | Voranate M-580 | 11.7 | 1.86 | 1.71 | — | 1 | — | — | — | — | 380 | 3.8 |
| 25. | Voranate M-580 | 35 | 5 | 4.6 | — | 1 | — | — | — | — | 380 | 8 |
| 26. | Voranate M-580 | 35 | 6.2 | 5.7 | — | — | — | 1 | — | — | 360 | 3.6 |

EDA - Ethylene diamine
DETA - Diethylene triamine
PDA - Propylene diamine
TEPA - Tetra ethylene penta amine

EXAMPLE 2

Stability of Unprotected Chlorpyrifos to UV/Visible Light

Unprotected chlorpyrifos was irradiated by an ultraviolet/visible light lamp for 68 hours. The stability versus the wavelength of the light is summarized as follows:

| Wave Lengths[a] | Extent of Degradation |
|---|---|
| 313 ± 5 | Total degradation |
| 365 ± 5 | Low degradation |
| 404 ± 5 | Low degradation |
| 436 ± 5 | Medium degradation |

[a]In nanometers

EXAMPLE 3

Metthod for Determining Acute Oral Toxicity with Mice

It is preferable lo use Adult males (2–2.5 months) weighing 25–30 g. A solution of the formulation was obtained by using a "Vortex" mixer for 5 min. The quantity of the solution depended on the weight of mouse. Thus, 1 ml. solution was administered for 20 g of mouse weight. The solution was introduced by using a syringe (2 ml) through the mouth into the stomach of mouse. The test was performed in 5 replications and mortality was checked after 0,5,24,72,96,120,144,168 hours. Standardized mouse food was given during the experiment. The results for three composition of the present invention are listed in Table 2 together with the data for a standard Emulsifiable Concentrate formulation of chlorpyrifos after a time of 168 hours.

TABLE 2

ID$_{50}$ ON MICE OF SEVERAL FORMULATIONS OF CHLORPYRIFOS

| | LD$_{50}$ | |
|---|---|---|
| Formulation[a] Number | Techincal Material[b] | Formulation of 250 g/l |
| 6 | 2250 | 9,000 |
| 13 | 2250 | 9,000 |
| 14 | >2700 | >10,800 |
| E.C. formulation | 120 | 480 |

[a]From Table 1
[b]mg/kg

EXAMPLE 4

Method for Determining the Susceptibility of Beetles (*Tribolium castaneum* and *Maladera matrida* to Insecticides)

This method was used to measure the levels of susceptibility of population of beetles to a given insecticide. The method was carried out in a room free from insecticide contamination. The beetles were treated and held at a temperature of 30° C. for *Tribolium castaneum* and 25° C. for *Maladera matrida* and a relative humidity above 25%. Beetles were obtained, as far as possible, from the same area, and kept in a suitable container until required; and they were given adequate and standardized food before the experiment, Adult beetles of either sex were used. *Tribolium castaneum* were grown on flour enriched with 1% of beer yeast. *Maladera matrida* were obtained from the land of the farm "Sufa" and held in the laboratory in a suitable container on the ground which was used for food. A solution of each of the different formulations and the commercial material was obtained by using a high-shear mixer for 5 min, For each formulation Whatman paper No. 41 (d=9 cm.) was dipped into the solution during mixing and put into a petri dish (d=9 cm). The filter paper for exposure time 0 was dried in the hood, and the others were taken to the roof of the laboratory and exposed to sunlight. Approximately every 5 days, 3 petri dishes were removed from the roof and 5 beetles were placed inside each dish by using an aspirator for *Trillium castaneum*. The experiment was performed in 3 replications and mortality was checked each replication. The results for *Maladera matrida* treated with various chlorpyrifos compositions are shown in Table 3.

TABLE 3

*Maladera matrida*
TREATED WITH VARIOUS CHLORPYRIFOS
MICROENCAPSULATED FORMULATIONS

| Exposure[a] | Concentration[c] | Percent Killed Formulation Type[b] | | | | |
|---|---|---|---|---|---|---|
| to sun | ppm | 14 | 13 | 6 | $EC_{45}$ | Blank |
| 0 | 500 | 100 | 100 | 100 | 100 | 0 |
| 6 |  | 86.7 | 100 | 100 | 53.3 |  |
| 10 |  | 80 | 93.3 | 93.3 | 53.3 |  |
| 17 |  | 6.7 | 0 | 33.3 | 0 |  |

[a]In days
[b]From Table 1
[c]Of chlorpyrifos

EXAMPLE 5

Method for Determining the Efficacy of Cockroaches (*Germanica blatella*) to Insecticides This method measured the levels of susceptibility of a population of cockroaches to Chlorpyrifos. Cockroaches were exposed to standard chlorpyrifos residues in a petri dish and mortality was determined. From the results, the times necessary for 50% and 95% knockdown ($LT_{50}$ and $LT_{95}$) can be determined. Adult males were used. If it was not feasible to obtain enough males, information on susceptibility can be obtained by using females. The test was carried out in a room free of insecticidal contamination. The cockroaches were exposed to the chlorpyrifos and held at a temperature between 25° C. and 30° C. and at a relative humidity above 25%. Cockroaches were given adequate and standardized food before the experiment. Cockroaches, *Germanica blatella* were grown in the laboratory in containers with ready-to-serve meaty dog food.

A solution of each of the different formulations and the commercial material was obtained by using a high-shear mixer for 5 min. A solution of different concentrations was prepared. For each formulation Whatman paper N41 (d=9) was dipped into the solution during mixing and put in a petri dish (d=9). The filter paper for exposure time was dried in a hood and the others were taken to the roof of the laboratory and exposed to sunlight. Approximately every 5 days a petri dish was removed from the roof, and 5 *Germanica blatella* cockroaches were placed inside. To introduce 5 cockroaches into each petri dish, the cockroaches was first anaesthetized with carbon dioxide. The test was performed in 3 replications and mortality was checked. The exposure times examined were 0,5,10,15 and 20 days, approximately. Control dishes—untreated Whatman paper with 5 cockroaches after 24 h. A cockroach was considered knocked down if it fails to move on being returned to a normal posture. The results for various microencapsulated formulations of chlorpyrifos are shown in Tables 4 and 5.

The tests were carried out according to the World Health Organization Technical Report Series No. 443 Geneva 1970, pp 130–133.

TABLE 4

*Germanicia blatella*
TREATED WITH VARIOUS CHLORPYRIFOS
MICROENCAPSULATED FORMULATIONS

| Exposure to Sun[a] | Formulation Type[b] | Percent Killed Concentration (ppm) | | | | | |
|---|---|---|---|---|---|---|---|
| | | 100 | 200 | 300 | 400 | 500 | Blank |
| 0 | 14 | 100 | 100 | 100 | 100 | 100 | 0 |
| 0 | 13 | 26.7 | 80 | 100 | 100 | 100 | |
| 0 | 6 | 0 | 93.3 | 93.3 | 93.3 | 100 | |
| 0 | EMPIRE[c] | 73.3 | 100 | 100 | 100 | 100 | |
| 0 | EW-20[d] | 100 | 100 | 100 | 100 | 100 | |
| 0 | EC-45[e] | 93.3 | 100 | 100 | 100 | 100 | |

[a]Hours
[b]From Table 1
[c]Dow Chemical Company microencapsulated chlorpyrifos, 200 g/l
[d]Water based formulation of Makhteshim Chemical Works.
[e]Standardized Emulsified Concentrate (non-microencapsulated) formulation of chlorpyrifos.

TABLE 5

*Germanicia blatella*
TREATED WITH VARIOUS CHLORPYRIFOS
MICROENCAPSULATED FORMULATIONS

| Exposure to sun[a] | Formulation Type[b] | Percent Killed Concentration (ppm) | | | | | |
|---|---|---|---|---|---|---|---|
| | | 25 | 50 | 100 | 150 | 200 | Blank |
| 0 | 14 | 100 | 100 | 100 | 100 | 100 | 0 |
| 0 | EMPIRE[c] | 26.7 | 33.3 | 53.3 | 80 | 100 | |
| 0 | EC-45[d] | 60 | 60 | 73.3 | 100 | 100 | |

[a]Hours
[b]From Table 1
[c]Dow Chemicals Company microencapsulated chlorpyrifos, 200 g/l
[d]Standardized Emulsified Concentrate (non-microencapsulated) formulation of chlorpyrifos.

EXAMPLE 6

Methhod for Determining Toxicity of Fish (Guppies)

All guppies require about the same basic care: water quality as close as possible to pH=7.0 (neutral); water temperature about 24°–25° C., and good strong light for least 12 hours a day (more light makes them grow faster). The test method was carried out in a room free of insecticidal contamination. Adult fish of either sex were used.

Guppies were obtained from a fish shop and kept in a suitable 16-liter aquariums (water temperature 23°–25° C.), 10 fish/aquarium, The guppies were given adequate and standardized food (Europet Basic Food) before and after the experiment. Food was withheld for 2 days before the experiment.

Solutions of formulation and commercial material were obtained by using a high-shear mixer for 5 min. Solutions 250,500,100,2000,4000,5000, μg/liter of the formulations were prepared. Mortality was checked after 3,6,24,48,72 and 96 hour. From the results, the times necessary for 50% and 95% mortality ($LT_{50}$ and $LT_{95}$) can be determined for each formulation. Test were carried out also on with golden orfe fish. The results are listed for golden orfe fish in Table 6.

TABLE 6

TOXICITY OF A CHLORPYRIFOS MICROENCAPSULATED FORMULATION TO GOLDEN ORFE FISH

| Time[a] | Concentration (μg/l) of Formulation 14 Percent Killed | | | | | EC (μg/l)[b] 250 |
|---|---|---|---|---|---|---|
| | 5000 | 2000 | 1000 | 250 | 50 | |
| | Percent Killed | | | | | |
| 0 | 0 | 0 | 0 | 0 | 0 | 0 |
| 3 | 100 | 0 | 0 | 0 | 0 | 0 |
| 6 | 100 | 0 | 0 | 0 | 0 | 10 |
| 24 | 100 | 30 | 10 | 0 | 0 | 10 |
| 48 | 100 | 40 | 20 | 0 | 10 | 30 |
| 72 | 100 | 40 | 20 | 10 | 10 | 30 |
| 96 | 100 | 40 | 20 | 10 | 20 | 30 |

[a]Hours
[b]Standardized Emulsified Concentrate (non-microencapsulated) formulation of chlorpyrifos.

EXAMPLE 1

Microencapsulated Chlorpyrifos using Variations of Formulation 14 and Containing Various Concentrations of Dyes Following the method of Example 1, one of the preferred microencapsulated formulation, Type 14 was prepared containing various different dyes. The microencapsulated formulations prepared are shown in Table 7.

TABLE 7

VARIATIONS OF FORMULATION TYPE 14 CONTAINING VARIOUS DYES

| Formulation Number | Isocyanate Type | Amount | EDA (g) | DETA (g) | Tinuvin 770 (g) | Colour type | amount (g) |
|---|---|---|---|---|---|---|---|
| 14-G | Voranate M-580 | 35 | 5.0 | 4.6 | 1 | Thermoplast green | 1 |
| 14-H | Voranate M-580 | 35 | 5.0 | 4.6 | 1 | Blue paste | 1 |
| 14-I | Voranate M-580 | 35 | 5.0 | 4.6 | 1 | Fluorescein | 1 |
| 14-J | Voranate M-580 | 35 | 5.0 | 4.6 | 1 | Sudan Blue | 1 |
| 14-K | Voranate M-580 | 35 | 5.0 | 4.6 | 1 | Macrolex Blue | 0.25 |
| 14-L | Voranate M-580 | 35 | 5.0 | 4.6 | 1 | Sudan III | 1 |
| 14-M | Voranate M-580 | 35 | 5.0 | 4.6 | 1 | Sudan III | 1 |
| 14-N | Voranate M-580 | 157.5 | 22.3 | 20.7 | 4.5 | Macrolex Blue | 1.5 |
| 14-O | Voranate M-580 | 259 | 36.7 | 34 | 7.7 | Macrolex Blue | 3.0 |
| 14-P | Voranate M-580 | 140 | 19.8 | 18.4 | 4 | Macrolex Blue | 1.6 |
| 14-Q | Voranate M-580 | 385 | 54.5 | 50.6 | 11 | Sudan Blue | 4.4 |
| 14-R | Voranate M-580 | 420 | 59.5 | 55.2 | 12 | — | — |
| 14-S | Voranate M-580 | 385 | 54.5 | 50.6 | 11 | Sudan Blue | 4.4 |
| 14-T | Voranate | 525 | 74.4 | 69 | 15 | Sudan Blue | 6 |

EXAMPLE 8

Following the method of Example 4, several microencapsulated formulations of chlorpyrifos were compared as to their effect against *Tribolium castaneum* in petri dishes after exposure to sunlight. Results are shown in Table 8.

TABLE 8

COMPARISON OF SEVERAL ENCAPSULATED FORMULATIONS ON
*TRIBOLIUM CASATANEUM* AFTER EXPOSURE TO SUNLIGHT
CONCENTRATION 500 P.P.M.

| Exposure to sun | Formulation type | | | | | | | | | | | | | |
|---|---|---|---|---|---|---|---|---|---|---|---|---|---|---|
| light days | EC | 14A | 14 | 13 | 21 | 19 | 2 | 3 | 4 | 5 | 6 | 8 | 9 | Penn phos. Penn wall |
| | | | | | | Percent Killed | | | | | | | | |
| 0 | 100 | 100 | 100 | 100 | 100 | 100 | 100 | 100 | 100 | 100 | 100 | 100 | 100 | 100 |
| 5 | 6 | 100 | 100 | 100 | 100 | 100 | 100 | 100 | 100 | 100 | 100 | 100 | 100 | 100 |
| 10 | 6 | 100 | 100 | 100 | 100 | 100 | 76 | 20 | 33 | 26 | 80 | 100 | 100 | 25 |
| 15 | 0 | 0 | 60 | 10 | 36 | 56 | 13 | 0 | 0 | 23 | 0 | 50 | 40 | 25 |

[a]EC

EXPERIMENT 9

Toxicity (Acute Contact and Oral $LD_{50}$) of Microencapsulated Chlorpyrifos to Honey Bees (*Apir mellifera* L.)

A. General

The study was performed with worker honey bees of about the same age, bred in a normal beekeeper's manner. For the tests, the bees were caught from the entrance hole of the hives in groups of ten with glass capture tubes, without anesthetics. During the tests, the bees were provided ad libritum with commercial ready to use syrup for honey bees as food. Stainless steel chambers (width 10 cm, height 8.5 cm, and depth 5.5 cm) served as test cages. The inner sides of the cages (except the front side) were covered with filter paper. The test cages were exposed in incubators at about 28° C., at 40 to 60% relative humidity in darkness, while being ventilated to avoid possible accumulations of pesticides vapor. The tests were performed in five dosages of microencapsulated chlorpyrifos and one solvent control with three replicates per dosage or control.

B. Contact Toxicity Test

First the test cages with the bees in it were exposed to $CO_2$ in an incubator to anaesthetize the test animals with $CO_2$ dosage chosen so that the anaesthetization was shorter that five minutes. The test substance was then applied to the anaesthetized bees; and the treated bees were then returned to the test cages and kept under test conditions for 48 hours. Five dosages of the test substances were tested in order to provide a rational base for a proper assessment of the control $LD_{50}$ of microencapsulated chlorpyrifos to honey bees. The anaesthetized bees are laid, ventral surface up, on filter paper in petri dishes. One μl drop per bee of microencapsulated chlorpyrifos in solvent was placed in the ventral thorax using a GC-syringe.

The result was an $LD_{50}$ contact of 22.1 μ/bee compared to a toxicity of 0.059 μ/bee for technical chlorpyrifos, C. Oral Toxicity Test Five dosages of microencapsulated chlorpyrifos in acetone were tested in order to provide a rational base for a proper assessment of the oral $LD_{50}$ to honey bees. Ten cages containing 10 bees each were prepared without food, letting the bees starve for 1 to 2 hours. Following this, 250 μl of the prepared solutions in type of Eppendorf-pipettes were hung in each cage through one of the top openings. The bees were observed as long as uptake of the solution takes place. Each bee that vomited the solution was excluded from the test. The bees were provided with normal food after the uptake of the tested solution, but at the latest after 3 hours.

The result was an $LD_{50}$ oral of 118.5 μ/bee compared to a toxicity of 0.25 μg/bee for technical chlorpyrifos.

EXAMPLE 10

Representative Preparation of the Microencapsulation of Endosulfan

Following the general method of Example 1 four solutions, A–D were prepared.

| | |
|---|---|
| Solution A: | 380 ml water |
| | 3.8 g polyvinyl alcohol (MOWIOL-G4) |
| Solution B: | 180 g melted endosulfan |
| | 42 g Voranate M-580 |
| | 1 g "TINUVIN-770" |
| | 1 g Irganox 1076 |
| Solution C: | 9 g water |
| | 9.3 g tetraethylinepentamine |
| | 5.6 g Diethylene triamine |
| Solution D: | 3.5 g propylene glycol |
| | 14.6 g Nonylphenol 6 moles ethoxylated (NP-6) |
| | 2.5 g xanthan gum |

Solution A is heated to 80° C. and Solution B is added and an emulsion is made using a high sheer mixer for 1–2 minutes. Solution C is then added and the reaction mixture is stirred for an additional 4 hours keeping the temperature of the mixture at 50° C. The pH of the solution is then reduced to 7.6 by adding $H_3PO_4$, Solution D is added, and the reaction mixture stirred for 15 minutes. Representative microencapsulated composition of endosulfan are listed in Table 9 and 10.

TABLE 9

| Sample Number | Isocyantes Type | Quantity (g) | Ethylene diamine (g) | Diethylene triamine (g) | U.V. absorber: (g) | Propylene- diamine (g) | Tetra- ethylene pent- amine: (g) | Propyl- ene gly- col: g | Nonyl- phenol 6 mole ethoxy- lated (NP-6) % | Xan- than gum (g) | Other add- itives | Conc. a.i. % |
|---|---|---|---|---|---|---|---|---|---|---|---|---|
| 31 | Voranate M-580 | 11.7 | 2.0 | 1.9 | Tinuvin 770 | — | — | 1.2 | 14.6 | 2.7 | — | 25.8 |
| 32 | Voranate M-580 | 11.7 | — | 1.9 | Active C | 2.6 | — | 1.5 | 14.6 | 2.7 | — | — |
| 33 | Voranate M-580 | 11.7 | 2.06 | 1.9 | Active C | — | — | 1.5 | 14.6 | 2.7 | — | — |
| 34 | Voranate M-580 | 11.7 | — | 1.9 | Active C | 2.6 | — | 1.5 | 14.6 | 2.7 | — | — |
| 35 | Isonate M-301 | 11.7 | 2.0 | 1.9 | Tinuvin 770 | — | — | 1.5 | 14.5 | 2.7 | — | — |
| 36 | Isonate M-301 | 11.7 | — | 1.9 | Tinuvin 770 | 2.6 | — | 1.5 | 14.6 | 2.7 | — | — |
| 37 | Voranate M-580 | 11.7 | 1.86 | 1.71 | Tinuvin 770 | — | — | 1.2 | 14.6 | 2.7 | — | 24 |
| 38 | Voranate M-580 | 11.7 | 1.86 | 1.71 | Tinuvin 770 | — | — | 1.2 | 14.6 | 2.5 | — | 25 |
| 39 | Voranate M-580 | 11.7 | 1.86 | 1.72 | Tinuvin 770 | — | — | 1.2 | 14.6 | 2.5 | — | 25 |
| 40 | Voranate M-580 | 35 | 5.6 | 5.3 | Tinuvin 770 | — | — | 3.5 | 14.6 | 2.5 | Ca(No$_3$)$_2$ | 17 |
| 41 | Voranate M-580 | 35 | 5.6 | 5.2 | Tinuvin 770 | — | — | 3.5 | 14.6 | 2.5 | — | — |
| 42 | Voranate M-580 | 35 | 5.6 | 5.3 | Tinuvin 770 | — | — | 3.5 | 14.6 | 2.5 | — | — |
| 43 | Voranate M-580 | 35 | 5.6 | 5.3 | Tinuvin 770 | — | — | — | — | 2.5 | — | — |
| 44 | Voranate M-580 | 35 | — | 5.3 | Tinuvin 770 | — | 8.69 | — | — | 2.5 | — | — |
| 45 | Voranate M-580 | 35 | — | 5.3 | Tinuvin 770 | 6.9 | — | — | — | 2.5 | — | — |
| 46 | Isonate M-301 | 35 | 5.6 | 5.3 | Tinuvin 770 | — | — | 3.5 | — | 2.5 | — | — |
| 47 | Voranate M-580 | 35 | — | — | Tinuvin 770 | 6.9 | 8.64 | 7.0 | 14.6 | 2.5 | — | — |
| 48 | Isonate M-301 | 35 | — | 5.3 | Tinuvin 770 | 6.9 | — | 3.5 | — | 2.5 | — | — |
| 49 | Voranate M-580 + TDI | 18 17 | — | 5.3 | Tinuvin 770 | — | 8.64 | 3.5 | 14.6 | 2.5 | — | — |
| 50 | HMDI | 26.1 | 5.6 | 5.3 | Tinuvin 770 | — | — | — | 14.6 | — | — | — |
| 51 | TDI | 26.1 | 5.6 | 5.2 | Tinuvin 770 | — | — | — | — | — | — | — |
| 52 | TDI | 26.1 | — | 5.7 | Tinuvin 770 | 7.7 | — | — | — | 2.5 | — | — |
| 53 | HMDI | 26.1 | — | 5.7 | Tinuvin 770 | 7.7 | — | — | 14.6 | — | — | — |

TABLE 10

| Sample Number | Isocyanates Type | Quantity | Amines Type | Quantity | Irganox 1076 gr. | Nonyl- phenol 6 mole ethoxy- lated (NP-6) | Xanthan gum | % a.i. |
|---|---|---|---|---|---|---|---|---|
| 54 | Isonate M-342 | 38.5 | DETA PDA | 5.0 6.8 | 1 | Solid additive | — | 19.4 |
| 55 | Voranate M-580 | 45.5 | DETA PDA | 5.93 8.06 | 1 | Solid additive | — | 21.3 |
| 56 | Voranate M-580 | 38.5 | DETA PDA | 5.01 6.8 | 1 | Solid | — | 23.8 |
| 57 | Voranate M-580 | 42 | DETA PDA | 5.7 7.4 | 1 | Solid Liquid | 14.8 2.5 | 26.0% |
| 58 | Voranate M-580 | 42 | DETA PDA | 5.57 9.54 | 1 | Solid Liquid | 14.8 2.5 | 30.7% |
| 59 | Isonate | 42 | DETA | 5.57 | 1 | Solid | 14.8 | 25.1% |

TABLE 10-continued

| Sample Number | Isocyanates Type | Quantity | Amines Type | Quantity | Irganox 1076 gr. | Nonyl-phenol 6 mole ethoxy-lated (NP-6) | Xanthan gum | % a.i. |
|---|---|---|---|---|---|---|---|---|
|  | M-342 |  | PDA | 7.4 |  | Liquid | 2.5 |  |
| 60 | Isonate | 42 | DETA | 5.57 | 1 | Solid | 14.8 | 25.2% |
|  | M-310 |  | TEPA | 9.3 |  | Liquid | 2.5 |  |
| 61 | Isonate | 42 | TEPA | 9.3 | 1 | Solid | 2.5 | 25.6% |
|  | M-342 |  | DETA | 5.57 |  | Liquid |  |  |

EXAMPLE 11

Following the method of Example 3, the two best microencapsulated formulations of the present invention containing endosulfan were listed for their toxicity to non-target species, represented by mice. The results are shown in Table 11. This shows the lower toxicity of formulation 61 as against formulation 59.

EXAMPLE 12

Following the method of Example 6, the two best microencapsulated formulations of the present invention containing endosulfan were tested for their toxicity to non-target species, fish, compared with the non-microencapsulated EC-35 formulation. The results are shown in Table 12. This shows the lower toxicity of formulation 61 as against both formulation 59 and against the non-microencapsulated EC-35 formulations of endosulfan.

TABLE 11

THE TOXICITY TO MICE OF THE TWO BEST MICROENCAPSULATED FORMULATIONS OF ENDOSULFAN[a]

| Exposure Time in Hours | Formulation No. 59 | | | | Formulation No. 61 | | | |
|---|---|---|---|---|---|---|---|---|
|  | Solution concentration - mg/kg | | | | | | | |
|  | 33.3 | 50 | 75 | 112.5 | 33.3 | 50 | 75 | 112.5 |
| 1 | 0 | 50 | 50 | 50 | 0 | 0 | 0 | 0 |
| 3 | 50 | 50 | 100 | 100 | 0 | 20 | 100 | 100 |
| 24 | 50 | 100 | — | — | 0 | 50 | — | — |
| 48 | 50 | — | — | — | 50 | 100 | — | — |
| 72 | 50 | — | — | — | 50 | — | — | — |
| 168 | 50 | — | — | — | 50 | — | — | — |

[a]Percent mortality.

TABLE 12

THE TOXICITY TO FISH OF THE TWO BEST MICROENCAPSULATED FORMULATIONS OF ENDOSULFAN[a]

| Exposure Time in hours | EC-35 | | | Formulation No. 59 | | | | | | Formulation No. 61 | | | | | |
|---|---|---|---|---|---|---|---|---|---|---|---|---|---|---|---|
|  | Solution concentration - mg/l | | | | | | | | | | | | | | |
|  | 1 | 5 | 10 | 2.5 | 5 | 8 | 16 | 50 | 100 | 2.5 | 5 | 8 | 16 | 50 | 100 |
| 3 | 0 | 0 | 30 | 0 | 0 | 0 | 0 | 0 | 0 | 0 | 0 | 0 | 0 | 0 | 0 |
| 6 | 0 | 0 | 30 | 0 | 0 | 0 | 10 | 10 | 0 | 0 | 0 | 0 | 0 | 0 | 0 |
| 24 | 0 | 57 | 70 | 0 | 20 | 20 | 40 | 43 | 100 | 0 | 0 | 0 | 0 | 20 | 50 |
| 48 | 0 | 57 | 100 | 0 | 20 | 30 | 40 | 71 | — | 0 | 0 | 30 | 30 | 30 | 100 |
| 72 | 0 | 57 | — | 0 | 20 | 30 | 40 | 71 | — | 0 | 0 | 30 | 30 | 40 | — |
| 96 | 0 | 57 | — | 0 | 20 | 30 | 40 | 71 | — | 0 | 0 | 30 | 30 | 40 | — |

[a]Percent mortality.

I claim:

1. A microencapsulated composition comprising particles having a shell consisting essentially of a polyurea and a pesticide encapsulated within said shell, said pesticide being selected from the group consisting of chlorpyrifos and endosulfan, and wherein said particles also comprise one or more photostable ultraviolet and visible light absorbent compounds having a log molar extinction coefficient of from about 2 to 5 with respect to radiation having wave lengths in the range of about 300 to 500 nanometers, said photostable ultraviolet and visible light absorbent compounds being selected from those which do not react with the monomer used in building the polyurea shell.

2. A composition in accordance with claim 1 wherein the photostable ultraviolet and and visible light absorbent compounds are selected from the group consisting of sterically hindered amines and dyes.

3. A composition in accordance with claim 2 wherein the sterically hindered amines are selected from the group consisting of "TINUVIN 770" and "TINUVIN 780".

4. A composition in accordance with claim 3 wherein the sterically hindered amine is "TINUVIN-770".

5. A composition in accordance with claim 2 wherein the dyes are selected are selected from group consisting of Thermoplast green, Blue paste Fluorescein, Sudan Blue, Macrolex blue and Sudan III.

6. A composition in accordance with claim 1 wherein the percentage of the envelope—excluding the water and polyvinyl alcohol—varies from 3% to 50%.

7. A composition in accordance with claim 6 wherein the percentage of the envelope—varies from 10% to 30%.

8. A composition in accordance with claim 1 wherein the fill contains from 0.57% to 5% of the photostable ultraviolet and visible light absorbent compound.

9. A composition in accordance with claim 8 wherein the fill contains from 1% to 3% of the photostable ultraviolet and visible light absorbent compound.

10. A composition in accordance with claim 1 having a high toxicity to target species while having a very low toxicity to non-target species, wherein said microcapsule particles are formed by interfacial polymerization.

11. A microencapsulated composition comprising a polyurea shell, chlorpyrifos and a photostable ultraviolet and visible light absorbent sterically hindered amine selected from the group having the trade names "TINUVIN 770" and "TINUVIN 780".

12. A composition in accordance with claim 11 wherein the sterically hindered amine is "TINUVIN-770".

13. A composition in accordance with claim 11 wherein the composition also contains dyes selected from the group consisting: of Thermoplast green, Blue paste Fluorescein, Sudan Blue, Macrolex blue and Sudan III.

14. A composition in accordance with claim 11 having a high toxicity to target species while having a very low toxicity to non-target species.

15. A microencapsulated composition comprising a polyurea shell, endosulfan, and a photostable ultraviolet and visible light absorbent sterically hindered amine selected from the group having the trade names "TINUVIN-770" and TINUVIN-780".

16. A composition in accordance with claim 15 wherein the sterically hindered amine is "TINUVIN-770".

17. A composition in accordance with claim 15 wherein the composition also contains dyes selected from the group consisting of Thermoplast green, Blue paste Fluorescein, Sudan Blue, Macrolex blue and Sudan III.

18. A composition in accordance with claim 15 having a high toxicity to target species while having, a very low toxicity to non-target species.

19. A composition in accordance with claim 2 wherein the percentage of the envelope—excluding the water and polyvinyl alcohol—varies from 3% to 50%.

20. A composition in accordance with claim 19 wherein the fill contains from 0.5% to 5% of the photostable ultraviolet and visible light absorbent compound.

* * * * *

UNITED STATES PATENT AND TRADEMARK OFFICE
CERTIFICATE OF CORRECTION

PATENT NO.   : 5,549,903
DATED        : August 27, 1996
INVENTOR(S)  : Arie Marcus It is certified that error appears in the above-indentified patent and that said Letters Patent is hereby corrected as shown below:

Cover page, column 1, after line [22], insert the following priority information:

--[30] March 3, 1994 [IL] Israel................ 108,835--

Signed and Sealed this

Eighteenth Day of February, 1997

Attest:

BRUCE LEHMAN

Attesting Officer      Commissioner of Patents and Trademarks